(12) United States Patent
Gifford (10) Patent No.: US 8,721,649 B2
(45) Date of Patent: May 13, 2014

(54) HIP JOINT ACCESS USING A CIRCUMFERENTIAL WIRE AND BALLOON

(75) Inventor: Hanson S. Gifford, Woodside, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 55 days.

(21) Appl. No.: 12/959,045

(22) Filed: Dec. 2, 2010

(65) Prior Publication Data

US 2011/0251619 A1  Oct. 13, 2011

Related U.S. Application Data

(60) Provisional application No. 61/266,931, filed on Dec. 4, 2009.

(51) Int. Cl.
*A61B 17/60* (2006.01)

(52) U.S. Cl.
USPC .......................................................... 606/90

(58) Field of Classification Search
USPC .......................................................... 606/90
See application file for complete search history.

(56) References Cited

U.S. PATENT DOCUMENTS

| | | | |
|---|---|---|---|
| 3,840,014 A | 10/1974 | Ling et al. |
| 3,875,595 A | 4/1975 | Froning |
| 4,467,479 A | 8/1984 | Brody |
| 4,669,106 A | 5/1987 | Ammerman |
| 4,772,266 A | 9/1988 | Groshong |
| 4,874,375 A | 10/1989 | Ellison |
| 4,928,670 A | 5/1990 | DeLorenzo |
| 4,968,316 A | 11/1990 | Hergenroeder |
| 4,983,165 A | 1/1991 | Loiterman |
| 4,995,875 A | 2/1991 | Coes |
| 5,019,042 A | 5/1991 | Sahota |
| 5,071,410 A | 12/1991 | Pazell |
| 5,171,297 A | 12/1992 | Barlow et al. |
| 5,176,683 A | 1/1993 | Kimsey et al. |
| 5,213,112 A | 5/1993 | Niwa et al. |
| 5,234,455 A | 8/1993 | Mulhollan |
| 5,290,220 A | 3/1994 | Guhl |
| 5,342,386 A | 8/1994 | Trotta |
| 5,344,459 A | 9/1994 | Swartz |

(Continued)

FOREIGN PATENT DOCUMENTS

| | | |
|---|---|---|
| DE | 25 01 080 | 7/1976 |
| EP | 0 507 645 | 10/1992 |

(Continued)

OTHER PUBLICATIONS

Ganz et al., Surgical dislocation of the adult hip, The Journal of Bone and Joint Surgery, Nov. 2001, vol. 83-B, No. 8, 1119-1124.

(Continued)

*Primary Examiner* — Nicholas Woodall
(74) *Attorney, Agent, or Firm* — Pandiscio & Pandiscio (57) ABSTRACT

The devices disclosed herein can provide access to the central compartment by accessing the medial-inferior side of the acetabulum, where a gap in the labrum exists. A distending device access the peripheral compartment of a hip joint. The device can then be circumferentially looped around the femoral head, and further tightened. Tightening the circumferential device can cause a balloon of the device to be placed within the gap. The balloon may then be inflated within the gap to distend the femoral head from the acetabulum.

21 Claims, 7 Drawing Sheets

(56) References Cited

U.S. PATENT DOCUMENTS

| | | | |
|---|---|---|---|
| 5,411,475 A | 5/1995 | Atala et al. | |
| 5,411,517 A | 5/1995 | Guignard | |
| 5,820,595 A | 10/1998 | Parodi | |
| 5,827,289 A | 10/1998 | Reiley et al. | |
| 5,827,318 A | 10/1998 | Bonutti | |
| 5,888,220 A | 3/1999 | Felt et al. | |
| 6,017,305 A | 1/2000 | Bonutti | |
| 6,123,718 A | 9/2000 | Tu et al. | |
| 6,171,236 B1 | 1/2001 | Bonutti | |
| 6,187,023 B1 | 2/2001 | Bonutti | |
| 6,217,548 B1 | 4/2001 | Tsugita et al. | |
| 6,468,289 B1 | 10/2002 | Bonutti | |
| 6,482,209 B1 | 11/2002 | Engh et al. | |
| 6,575,979 B1 | 6/2003 | Cragg | |
| 6,616,673 B1 * | 9/2003 | Stone et al. | 606/105 |
| 6,620,181 B1 | 9/2003 | Bonutti | |
| 6,855,149 B2 | 2/2005 | Dye | |
| 6,859,661 B2 | 2/2005 | Tuke | |
| 6,860,892 B1 | 3/2005 | Tanaka et al. | |
| 7,166,121 B2 | 1/2007 | Reiley et al. | |
| 7,189,229 B2 | 3/2007 | Lopath et al. | |
| 7,201,756 B2 | 4/2007 | Ross et al. | |
| 7,216,385 B2 | 5/2007 | Hill | |
| 7,217,273 B2 | 5/2007 | Bonutti | |
| 7,226,462 B2 | 6/2007 | Tanaka et al. | |
| 7,241,303 B2 | 7/2007 | Reiss et al. | |
| 7,488,337 B2 | 2/2009 | Saab et al. | |
| 2001/0001128 A1 | 5/2001 | Holman et al. | |
| 2001/0001315 A1 | 5/2001 | Bates et al. | |
| 2002/0177866 A1 | 11/2002 | Weikel et al. | |
| 2003/0004460 A1 | 1/2003 | Bedell | |
| 2003/0033017 A1 | 2/2003 | Lotz et al. | |
| 2003/0220698 A1 | 11/2003 | Mears et al. | |
| 2004/0059290 A1 | 3/2004 | Palasis | |
| 2004/0106861 A1 | 6/2004 | Leitner | |
| 2004/0116848 A1 | 6/2004 | Gardeski et al. | |
| 2004/0138754 A1 | 7/2004 | Lang et al. | |
| 2004/0236342 A1 | 11/2004 | Ferree et al. | |
| 2005/0267482 A1 | 12/2005 | Hyde, Jr. | |
| 2006/0015171 A1 | 1/2006 | Armstrong | |
| 2006/0184246 A1 | 8/2006 | Zwirkoski | |
| 2006/0259063 A1 | 11/2006 | Bates et al. | |
| 2006/0293685 A1 | 12/2006 | Stone et al. | |
| 2006/0293750 A1 | 12/2006 | Sherman et al. | |
| 2007/0173946 A1 | 7/2007 | Bonutti | |
| 2007/0213759 A1 | 9/2007 | Osborne et al. | |
| 2007/0219561 A1 | 9/2007 | Lavallee et al. | |
| 2007/0255394 A1 | 11/2007 | Ryan | |
| 2007/0265635 A1 | 11/2007 | Torrie et al. | |
| 2008/0019004 A1 | 1/2008 | Hansen | |
| 2008/0045967 A1 | 2/2008 | Lubinus et al. | |
| 2008/0109004 A1 | 5/2008 | Da Rold et al. | |
| 2009/0112214 A1 * | 4/2009 | Philippon et al. | 606/90 |
| 2009/0299282 A1 | 12/2009 | Lau et al. | |
| 2009/0312807 A1 * | 12/2009 | Boudreault et al. | 606/86 R |
| 2010/0312179 A1 * | 12/2010 | Nikolchev et al. | 604/96.01 |

FOREIGN PATENT DOCUMENTS

| | | |
|---|---|---|
| FR | 1 061 009 | 4/1954 |
| FR | 2 734 146 | 11/1996 |
| WO | WO 92/22259 | 12/1919 |
| WO | WO 97/27897 | 8/1997 |
| WO | WO 99/59669 | 11/1999 |
| WO | WO 00/23009 | 4/2000 |
| WO | WO 01/45601 | 6/2001 |
| WO | WO 2005/048812 | 6/2005 |
| WO | WO 2007/080454 | 7/2007 |
| WO | WO 2007/092841 | 8/2007 |
| WO | WO 2009/042429 | 4/2009 |
| WO | WO 2010/097724 | 2/2010 |
| WO | WO 20101107949 | 9/2010 |

OTHER PUBLICATIONS

Aydin et al., A New Noninvasive Controlled intra-articuiar Ankle Distraction Teohnique on a Cadaver Model; Arthroscopy: The Journal of Arthroscopic and Related Surgery, Aug. 2006. vol. 22, No, 8, 905,e1-905.e3.

Burman, Arthroscopy or the Direct Visualization of joints: An Experimental Cadaver Study, The Journal of Bone and Joint Surgery, Oct. 1931, vol. XIII, No. 4., 669-695.

Dienst, Chapter 11: Hip Arthroscopy Without Traction, 2005, pp. 170 and 174.

Dienst et al., Hip Arthroscopy Without Traction: In Vivo Anatomy Of The Peripheral Hip Joint Cavity, Arthroscopy: The Journal of Arthroscopic and Related Surgery, Nov.-Dec. 2001, vol. 17, No. 9, 924-931.

Sartoretti et al., Angioplasty Balloon Catheters Used for Distraction of the Ankle Joint, Arthroscopy: The Journal Of Arthroscopic And Related Surgery, Feb. 1996, vol. 12, No. 1, 82-86.

Shetty et al., Hip arthroscopy: current concepts and review of literature, Br J Sports Med, 2007, 41, 64-68.

Tan et al., Contribution Of Acetabular Labrum To Articulating Surface Area And Femoral Head Coverage In Adult Hip Joints: An Anatomic Study In Cadavera, The American Journal of Orthopedics, Nov. 2001, vol. XXX, No. 11, 809-812.

Dienst et al, Effects of Traction, Distension, and Joint Position on Distraction of the Hip Joint: An Experimental Study in Cadavers, Arthroscopy: The Journal of Arthroscopic and Related Suroery, Oct. 2002, vol. 18, No. 18, 865-671.

Byrd, Operative Hip Arthroscopy, 2005, 146-147.

* cited by examiner

HIP JOINT ACCESS USING A CIRCUMFERENTIAL WIRE AND BALLOON

REFERENCE TO PENDING PRIOR PATENT APPLICATION

This patent application claims benefit of prior U.S. Provisional Patent Application Ser. No. 61/266,931, filed Dec. 4, 2009 by Hanson S. Gifford for HIP JOINT ACCESS USING A CIRCUMFERENTIAL WIRE AND BALLOON.

FIELD OF THE INVENTION

The present invention relates to medical devices and methods for accessing a joint, and more specifically to devices and methods for providing minimally invasive access into the central compartment of a hip joint.

BACKGROUND OF THE INVENTION

Obtaining arthroscopic access into orthopedic joints to perform surgical procedures can be extremely challenging. This is particularly true of the hip joint, which has two tissue barriers that must be crossed in order to gain access to the inner part of the joint. The outer barrier is known as the capsule, a series of tight overlapping ligaments surrounding the joint. The area within the capsule is known as the peripheral compartment.

Within the peripheral compartment, the joint is fluidly sealed by a skirt-like tissue known as the labrum which is attached to the acetabular rim and hugs tightly around the base of the femoral head. The labrum/femoral head interface creates a vacuum seal within the joint which helps to hold the femoral head tightly within the acetabulum. In order to gain access to the central compartment (i.e., the portion of the joint within the labrum lying between the femoral head and acetabulum) the seal of the labrum must be broken and instruments then introduced into the very narrow opening between the bottom edge of the labrum and femoral head.

In arthroscopic surgery, access to the peripheral compartment is typically obtained through the use of elongate tubular devices (e.g., arthroscopic portals or cannulas), which are inserted through the patient's skin and through the ligaments of the capsule so as to provide a tunnel or lumen through which instruments may be introduced. Two to three such portals are typically employed, one being used for placement of an arthroscope, and the remaining portal(s) being available for the introduction of other instruments.

In order to gain access to the central compartment, surgeons typically use a distraction table, a surgical table that includes a post placed against the patient's perineum and a tensioning device which fastens to the patient's foot or ankle and allows high forces to be exerted on the patient's leg to distract the femur and create space within the joint. These tables not only are large, cumbersome and expensive, but they limit the mobility of the joint during the procedure and frequently produce complications such as nerve damage.

Methods and devices have been proposed for distracting the hip joint without using a distraction table. For example, co-assigned U.S. patent application Ser. No. 12/483,446, filed June 1/2/2009, entitled "Methods and Apparatus for Joint Distraction", the entirety of which is incorporated by reference herein, discloses various internal distraction devices for distracting the hip and other joints. These devices use balloons or other expandable features placed within the central compartment to displace the femoral head further away from the acetabulum in order to allow access for surgical instruments. Such devices may also require insertion between areas where the labrum meets the femoral head. While such devices eliminate the need for a distraction table, challenges may still be encountered in introducing these devices into the peripheral and central compartments.

SUMMARY OF THE INVENTION

One embodiment of the invention provides a method for distracting a femoral head from an acetabulum of a hip joint. The interior of a capsule surrounding the femoral head and acetabulum may be accessed, the acetabulum being moveably sealed to the femoral head by a labrum. A device may be looped around the femoral head. A balloon of the device may be guided to a gap in the labrum. The device may be tightened to force the balloon into the gap. The balloon may then be inflated to distract the femoral head from the acetabulum.

Another embodiment of the invention provides a device for distracting a femoral head from an acetabulum of a hip joint. The device may include a shaft with a distal end and a proximal end. An elongated wire may be slidably housed within the shaft. The elongated wire may have a distal loop and a balloon located on a mid-portion of the elongated wire.

In one preferred form of the invention, there is provided a method for distracting a femoral head from an acetabulum of a hip joint, comprising:

accessing the interior of a capsule surrounding the femoral head and acetabulum, the acetabulum being moveably sealed to the femoral head by a labrum;

looping a device around the femoral head;

guiding a balloon of the device to a gap in the labrum;

tightening the device to place the balloon into the gap; and inflating the balloon to distract the femoral head from the acetabulum.

In another preferred form of the invention, there is provided a device for distracting a femoral head from an acetabulum of a hip joint, comprising:

a shaft with a distal end and a proximal end; and an elongated wire slidably housed within the shaft, the elongated wire having a distal loop and a balloon located on a mid-portion of the elongated wire.

These and other embodiments are described in further detail in the following description related regarding the following figures.

DETAILED DESCRIPTION OF THE INVENTION

Devices and methods are disclosed regarding accessing the central compartment of a hip joint via the medial-inferior side of the acetabulum. The devices disclosed herein can be generally used after access has been established into the capsule (i.e., peripheral compartment) of a hip joint. Two to three portals may be established which penetrate a patient's skin and capsule. The devices disclosed herein can use these portals to gain further access to the central compartment.

The devices disclosed herein can provide access to the central compartment by accessing the medial-inferior side of the acetabulum, where a gap in the labrum exists. A distending device can be looped around the femoral head, and further tightened. The device may include a balloon which is placed within the gap when the device is tightened. The balloon may then be inflated within the gap to distend the femoral head from the acetabulum. The device may include additional balloons to further distend the femoral head from the acetabulum. The devices and methods disclosed herein can be used in a minimally invasive manner in conjunction with known arthroscopic visualization systems and/or other visualization systems such as fluoroscopy.

Figure 1:
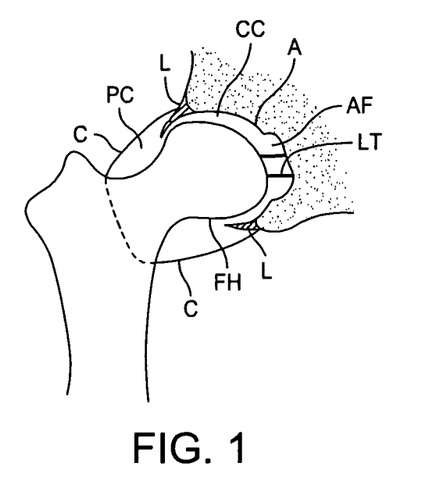
FIG. 1 is a simplified cross-sectional view of a hip joint.

FIG. 1 illustrates the basic anatomy of a hip join. In FIG. 1 the hip joint is formed between the head of the femur FH and the acetabulum A, a concave surface of the pelvis. The acetabular fossa AF is a recessed region in the acetabulum. A blanket of ligaments covers the joint forming a capsule C. Additionally, the acetabular labrum L, a fibrocartilaginous lip, surrounds the head of the femur, deepens the joint pocket and increases the surface area of contact. Labrum L divides the hip joint into two compartments within the joint capsule: a central compartment CC and a peripheral compartment PC. Central compartment CC is within the confines of labrum L and contains the majority of the joint cartilage and the ligamentum teres LT, a ligament attached to a depression in the acetabulum (the acetabular notch or fossa) and a depression on the femoral head (the fovea of the head). Peripheral compartment PC is everything outside the labrum. The central compartment CC is not visible until the joint has been distracted.

Figure 2:
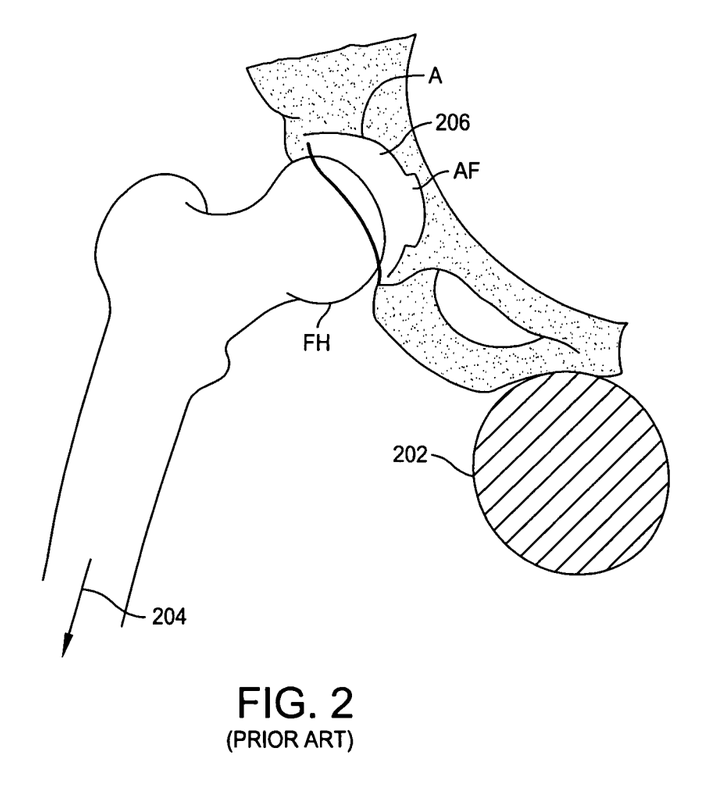
FIG. 2 is a simplified cross-sectional view of a hip joint undergoing a prior art method for distracting a femoral head from an acetabulum.

FIG. 2 illustrates how traction 204 is conventionally applied to the patient's leg and against a post 202 positioned against the perineum region to distract the femoral head FH away from the acetabulum A, thereby creating a space 206 between the two joint surfaces. This space 206 allows a surgeon to access the joint and perform diagnostic or therapeutic procedures. However, conventional distraction tables are often rigid systems affixed to an operating room table and they are not easily adjustable. Thus, once distraction is obtained, conventional distraction tables are locked into position to maintain the distraction and have very limited capability for further manipulation of the joint to provide greater access to the joint or access to different regions of the joint space. For example, in the case of a hip joint, it would be desirable to be able to flex, extend, abduct, adduct, laterally rotate or medially rotate the joint through a broad range of motion so that access and visibility to the joint space and adjacent structures may be adjusted while the joint is distracted. In addition, even with distraction tables that allow some manipulation of the hip joint, because traction must be maintained, it is not possible using conventional distraction tables to bend the patient's knee. When the leg is straight, the hip joint may be flexed up to approximately 20°, but bending the knee allows the hip joint to be flexed even more, thereby allowing even greater access to the joint. Additionally, the pressure exerted by post 202 against the perineum can result in post operative complications and therefore it would be desirable to provide improved methods and devices for distraction of joints.

Figure 3:
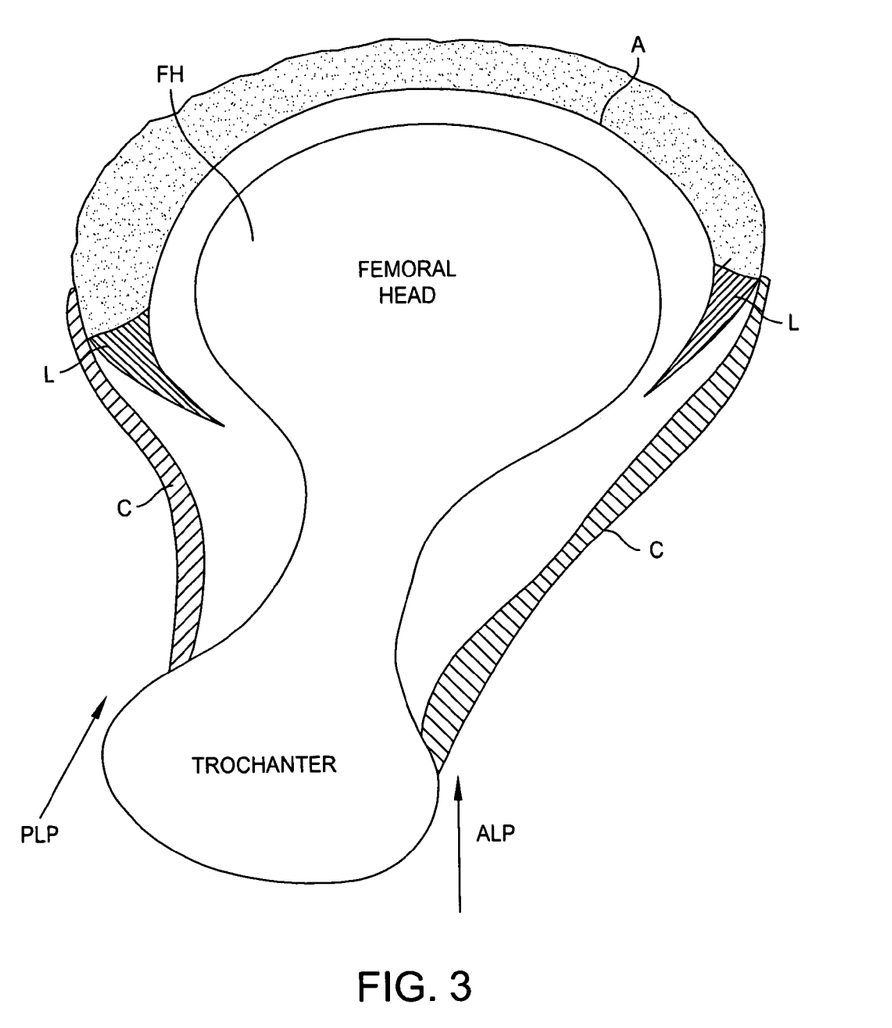
FIG. 3 is a simplified cross-sectional view of a hip joint.

FIG. 3 illustrates some of the possible entry portals for delivering a balloon to the hip joint. FIG. 3 is a top view of a hip joint in which the femoral head FH rests against the acetabulum A. The joint space is covered by capsule C and labrum L. Access to the hip may be obtained by introducing a balloon in a posterolateral portal PLP along, a side and posterior to the joint or an anterolateral portal ALP along a side and anterior to the joint. The balloon and related instruments may be delivered into the joint space through a port or cannula, or using minimally invasive techniques such as Seldinger-like or percutaneous introduction, or a cutdown procedure may be used.

FIGS. 4A-4F show a device for separating the femoral head FH from the acetabulum A.

Figure 4A:
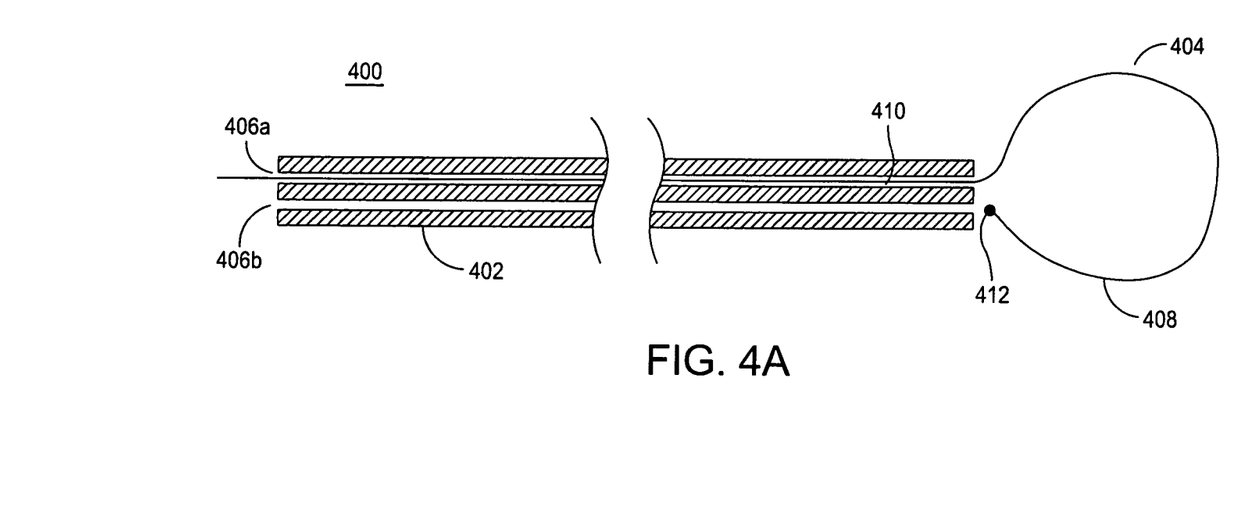
FIG. 4A is a cross-sectional view of a device for separating a femoral head from an acetabulum, according to an embodiment of the invention.

As shown in FIG. 4A, device 400 can include an elongated shaft 402 and an elongated wire 404, which is slidably housed within device 400. Shaft 402 may have at least one lumen, and as shown includes a feeding lumen 406a and a return lumen 406b. More than two lumens may also be used. Shaft 402 may have a circular cross-section, although other shapes can also be used, for example, oval, square, or triangular. Shaft 402 may have an outer diameter ranging from 0.04-0.20 inches, to allow insertion into standard arthroscopy portals. Shaft 402 may have a wall thickness ranging from 0.005-0.020 inches. Shaft 402 may be constructed from a relatively stiff alloy, such as stainless steel, or from a polymer, such as extruded nylon or PET. The distal end of shaft 402 can include a metal reinforcing ring, to prevent splitting. Shaft 402 may also be constructed from a super elastic material, such as a nickel-titanium alloy. Feeding lumen 406a and return lumen 406b can have circular cross-sections with diameters ranging from 0.01-0.10 inches. Feeding lumen 406a and return lumen 406b may have other cross-sections besides circular, for example, semi-circular or pie-wedge. Feeding lumen 406a and return lumen 406b can have differently sized and shaped cross-sections. The distal portion of shaft 402 may be coupled to a roller or sliding mechanism which can provide tension to both ends of the elongated wire (not shown).

Elongated wire 404 may include a pre-curved distal loop 408 and a straight section 410. Elongated wire 404 can have shape-memory characteristics. For example, distal loop 408 can be forcibly elongated and slidably constrained in feeding lumen 406a, and resume the shape as shown upon exiting feeding lumen 406a. Distal loop 408 can have a diameter ranging from 0.75-3.0 inches. Elongated wire 404 may also have an atraumatic tip 412, which may be configured as a bail. Atraumatic tip 412 may also be formed from a soft material, relative to the hardness of surfaces of the hip joint, such as a plastic. Automatic tip 412 may also be ferrous or magnetic. Elongated wire 404 can have a circular cross-section with a diameter ranging from 0.002-0.100 inches. Elongated wire 404 can also have a non-circular cross-section, for example, rectangular. Elongated wire 404 may be constructed from a flexible alloy such as stainless steel, or a super elastic nickel-titanium alloy. Elongated wire 404 may be coated with a lubricous material such as PTFE.

Figure 4B:
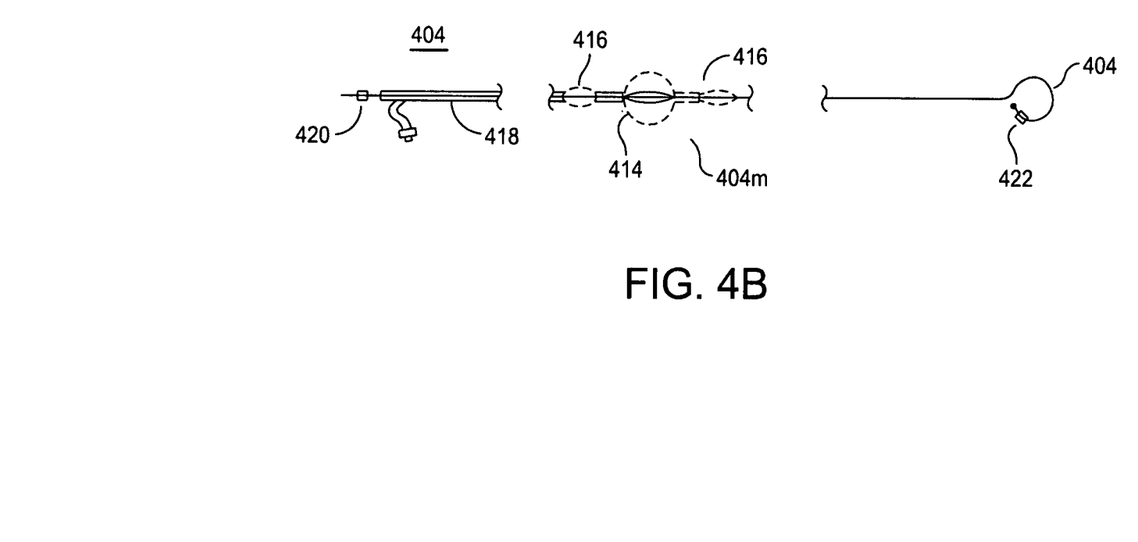
FIG. 4B is a side view of an elongated wire for use with the device of FIG. 4A, according to an embodiment of the invention.

As shown in FIG. 4B, a mid-portion 404m of elongated wire 404 may include a distending device, such as a balloon 414. Additional balloons 416 may also be placed distally and proximally to balloon 414. Balloon 414 may be constructed from a non-compliant (e.g., 0-10% compliance range) thin-walled material such as PET, or from a semi-compliant (e.g., 10-20% compliance range) thin-walled material; such as PET; nylon, and polyurethane. The balloon may be capable of withstanding high pressures (e.g., up to 400 psi), and include reinforcement features, such as integrated woven fibers, to help prevent bursting. Balloon 414 can have a wall thickness ranging from 0.0001-0.008 inches. Balloon 414 is shown in an expanded configuration and may have an expanded diameter of 2-40 mm. Balloon 414 may utilize various shapes and sizes other than the generally cylindrical shape shown, such as spherical, and shapes which are tailored to fit within acetabulum A and acetabular fossa AF, such as curved or kidney-shaped balloons.

Balloon 414 is fluidly coupled to an elongated catheter 418, which can include a lumen to house elongated wire 404 and for supplying fluidic pressure to balloon 414. Elongated catheter 418 can be constructed from extruded plastic tubing, such as nylon or PET. Elongated catheter 418 can include a proximal fitting (e.g., Luer) for coupling to a pressure source, such as a hand pump. Balloon 414 can be bonded or heat formed to elongated catheter 418. Balloon 414 may be folded in an unexpanded configuration to have an effective diameter which is roughly equivalent to the outer diameter of elongated catheter 418 which can have an outer diameter ranging from 0.02-0.10 inches. The cross-sectional shape of elongated catheter 418 may be the same as feeding lumen 406a.

Elongated wire 404 can also include a proximal marker 420 and a distal marker 422. Proximal marker 420 and distal marker 422 can be color indicative marks, collars, or any visual feature. Proximal marker 420 and distal marker 422 can be equally spaced from the center of balloon 414 along the length of elongated wire 404, including along the circumference of distal loop 408.

Figure 4C:
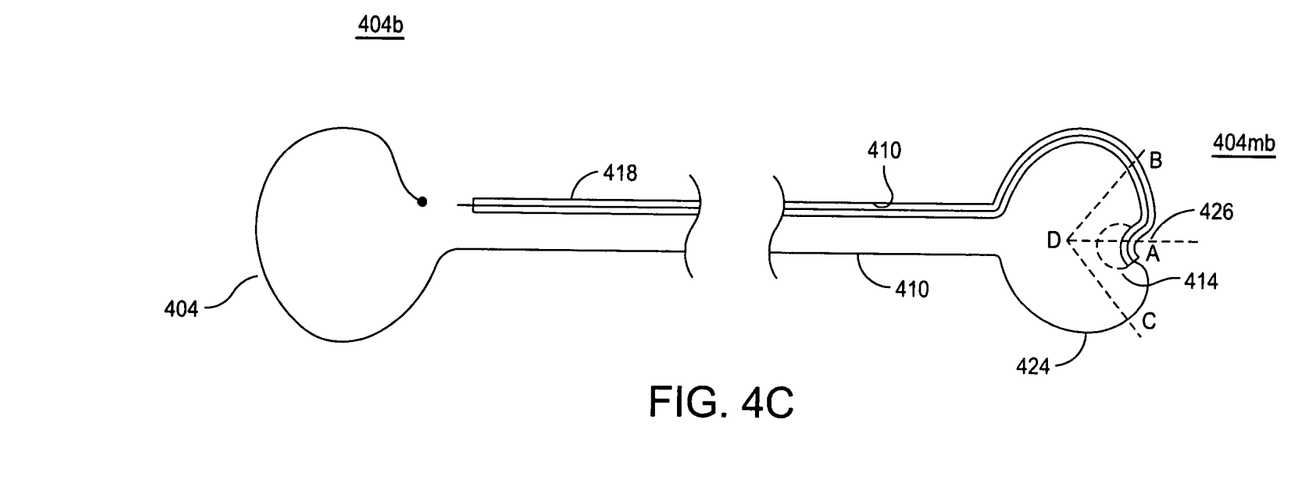
FIG. 4C is a side view of an alternative elongated wire for use with the device of FIG. 4A, according to an embodiment of the invention.

FIG. 4C shows an alternative elongated wire 404b. Elongated wire 404b is constructed similarly to elongated wire 404. However, elongated wire 404b can include a center loop 424 at a mid-section 404mb. Center loop 424 can have a circular shape with a diameter ranging from 0.75-3.0 inches. Center loop 424 can also be configured as other shapes, for example, a U shape or M shape. Balloon 414 can be centrally located on center loop 424 at point A and aligned between straight sections 410 of elongated wire 404b. Balloon 414 can also be located at different points of center loop 424, for example points B or C. If desired, points B and C can also include additional balloons 416 (not shown in FIG. 4C, but shown in FIG. 4B). Center loop 424 can include a notch 426 which can bias balloon 414 towards a center D of center loop 424. Balloon 414 can also be biased to inflate towards the center of center loop 424, as shown by the dashed outline. Center loop 424 can be forcibly elongated by constraining within feeding lumen 406a, and resume the shape as shown upon exiting feeding lumen 406a.

Figure 4D:
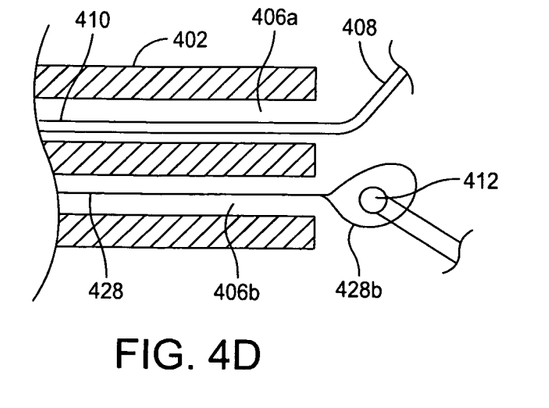
FIGS. 4D-4F are cross-sectional views of a distal portion of the device of FIG. 4A and various recapturing devices, according to embodiments of the invention.

FIG. 4D shows the distal tip of shaft 402 including a recapturing device configured as an elongated snare 428. Elongated snare 428 can be sized to slide within return lumen 406b. The elongated snare can be constructed from a metal or polymer wire. Elongated snare 428 can include a snare loop 428b, which can be sized to capture atraumatic tip 412. The proximal end of elongated snare 428 can be coupled to a mechanism for actuation, such as a slider or gear driven wheel (not shown).

Figure 4E:
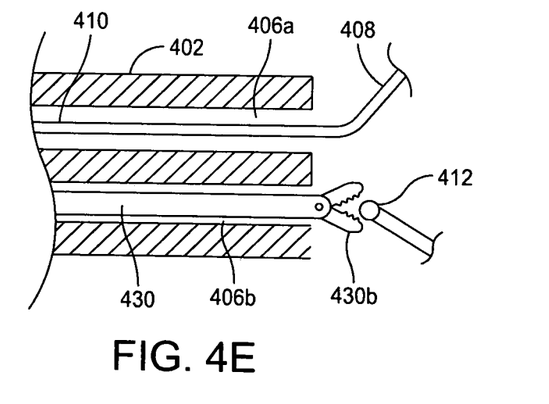

FIG. 4E shows the distal tip of shaft 402 including a recapturing device configured as a grasper 430. Grasper 430 can be sized to slide within return lumen 406b. Grasper 430 can include graspers 430b which are hinged to grasper 430. Grasper 430 can be physically integrated to device 400, or be a separate device, such as a commercially available biopsy grasper. Grasper 430 can be actuated to grasp atraumatic tip 412.

Figure 4F:
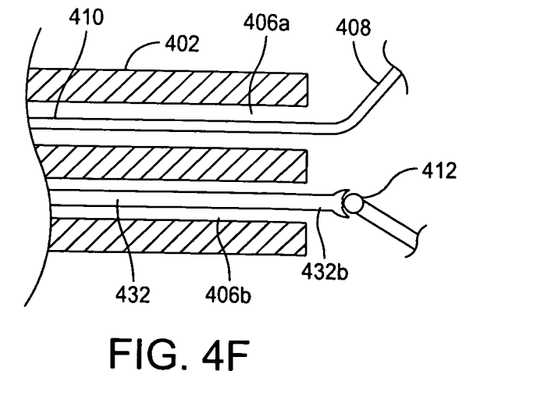

FIG. 4F shows the distal tip of shaft 402 including a recapturing device configured as an elongated socket 432. Elongated socket 432 can be sized to slide within return lumen 406b. Elongated socket 432 can include a distalmost socket 432b which can comprise a magnet, such as a neodymium magnet. Distalmost socket 432b can magnetically couple to atraumatic tip 412, which can also be magnetic. Elongated socket 432 can be constructed from a metal or polymer wire/tube. The proximal end of the elongated socket can be coupled to a mechanism for actuation, such as a slider or gear driven wheel (not shown).

FIGS. 5A-5D show a method of using device 400 to distract the femoral head from acetabulum A. FIGS. 5A-5D shows lateral facing views of acetabulum A. The femoral head FH extends normally from this view, hut is not shown for clarity. A portal P has been placed within capsule C to provide access to peripheral compartment PC. A gap G exists in the labrum L on the medial-inferior side of the acetabulum, and is blocked by femoral head FH. Portal P can be brought into alignment with gap G.

Figure 5A:
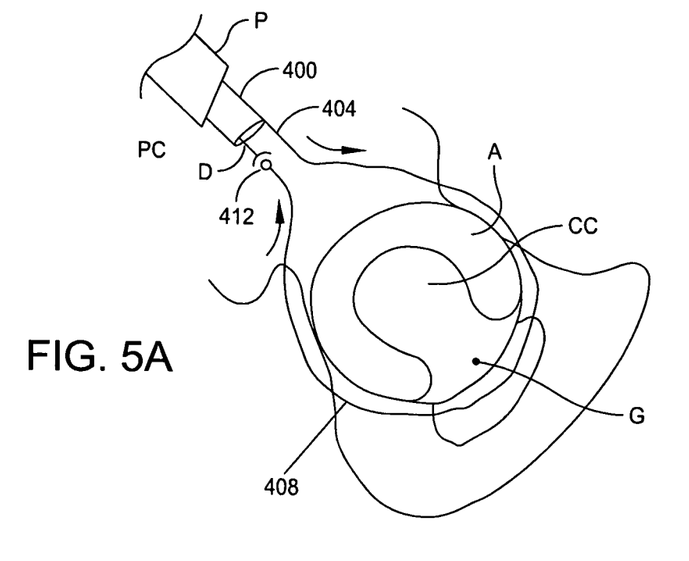
FIGS. 5A-5D show lateral facing views of the acetabulum of a hip joint, undergoing a method for distracting a femoral head from an acetabulum, according to embodiments of the invention.

Referring to FIG. 5A, device 400 can access peripheral compartment PC through portal P. Elongated wire 404 can then be advanced out of device 400 as shown by the indicative arrows. Distal loop 408 can reform from a straightened shape to a circumferential shape, when being advanced out of device 400. Due to the shape of distal loop 408, advancing device 400 causes device 400 to loop around femoral head FH, as shown. Atraumatic tip 412 is routed around femoral head FH and positioned at the distal end of device 400. A capturing device D for recapturing atraumatic tip 112 is also advanced out of device 400 and can couple to atraumatic tip 412. The device can be snare 428, grasper 430, elongated socket 432 or another capturing device. After coupling to atraumatic tip 412, the coupled recapturing device D can be withdrawn back into device 400, which re-straightens distal loop 408. Withdrawing distal loop 408 into the device 400 causes balloon 414 to advance to the distal end of device 400.

Figure 5B:
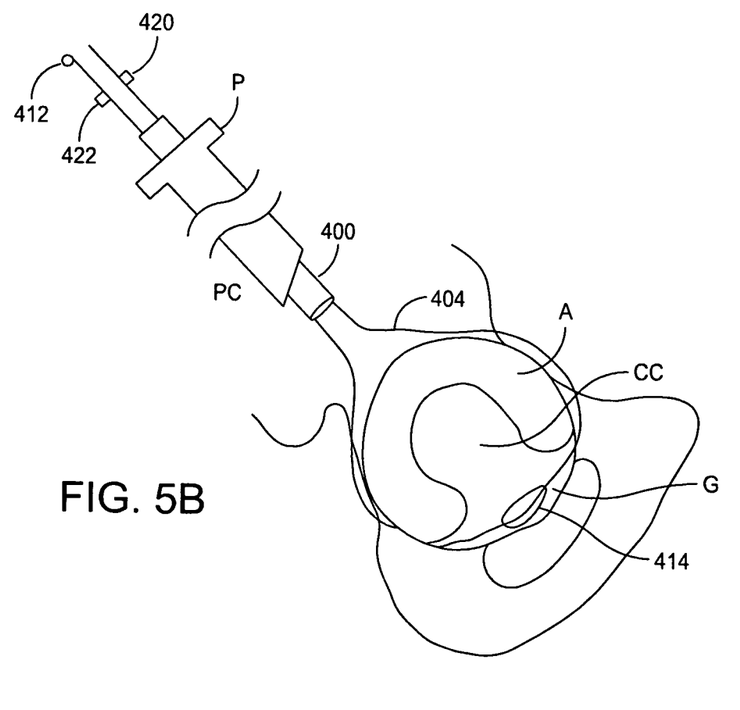

Referring to FIG. 5B, distal loop 408 can be withdrawn back into device 400 until proximal marker 420 and distal marker 422 are aligned. Aligning the markers causes balloon 414 to be guided to the vicinity of gap G, as proximal marker 420 and distal marker 422 can be equally spaced from balloon 414.

Figure 5C:
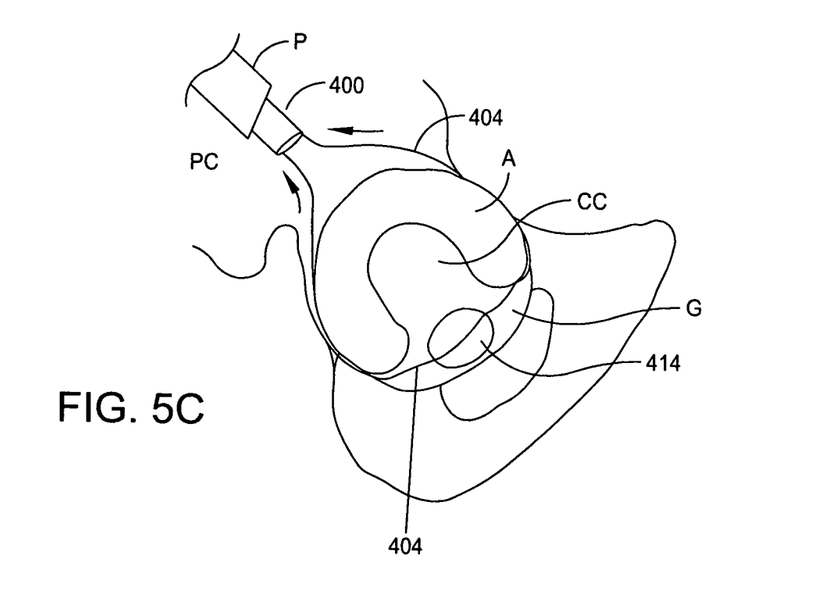

Referring to FIG. 5C, elongated wire 404 can be tightened, equally from both the distal and proximal ends of elongated wire 404, as shown by the indicative arrows. Tightening elongated wire 404 causes the circumferential portion of elongated wire 404 around femoral head FH to reduce in size as it draws down on the spherical outer surface of femoral head FH. Accordingly, tightening the wire can cause balloon 414 to be drawn into and placed within gap G. Elongated wire 404 should be tightened between the equator of femoral head FH and acetabulum A, to assure balloon 414 is drawn down to gap G. The femur can be manipulated to place the equator of femoral head FH in an optimum position before tightening elongated wire 404. Elongated wire 404 can be clamped by an integral device or external clamps to maintain tension of elongated wire 404 and balloon 414 in gap G. Once balloon 414 is secured into gap G, balloon 414 may be inflated to distract acetabulum A from femoral head FH.

Alternatively, elongated wire 404b of FIG. 4C can be used. Center loop 424 can be tightened when notch 426 is aligned with gap G. Due to the shape of notch 426, balloon 414 may be placed deeper into gap G for better distraction capability. Notch 426 can also serve as a balloon alignment tool using physical feedback when advancing and/or tightening wire 404b, as notch 426 can have the tendency to engage gap G. For example, pushing and pulling on wire 404b may become more noticeably difficult when notch 426 is within the gap. Thus, the increased difficulty can confirm that notch 426 is aligned in gap G.

Figure 5D:
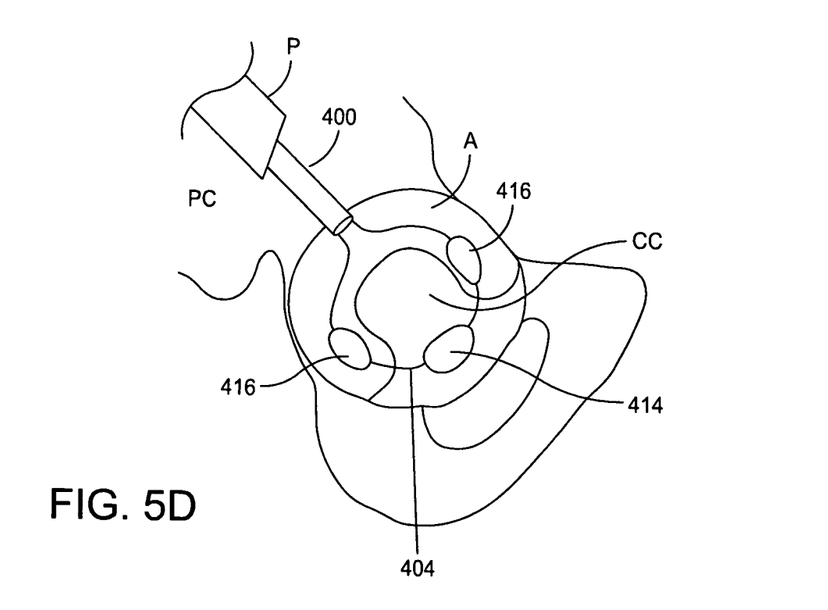

Referring to FIG. 5D, elongated wire 404 can be drawn from the sides of central compartment CC after femoral head FH is separated from acetabulum A, as the labrum (not shown in FIG. 5D) can then be fully separated around the entire circumference of femoral head FH. After balloon 414 has been inflated, elongated wire 404 may be relaxed to push the wire portions extending from balloon 414 out of central compartment CC, to allow for better access to portions of central compartment CC by other surgical devices. Alternatively, or additionally, after balloon 414 has been inflated, elongated wire 404 may be tightened further to pull the wire portions extending from balloon 414 inwards and away from labrum L, to allow for better access to portions of central compartment CC by other surgical devices. If optional balloons 416 are present, balloons 416 can also be inflated to further distract acetabulum A from femoral head FH.

After the desired surgical procedure within central compartment CC has been completed, ball 414 can be deflated and elongated wire 404 can be withdrawn back into device 400.

MODIFICATIONS OF THE PREFERRED EMBODIMENTS

It should be understood that many additional changes in the details, materials, steps and arrangements of parts, which have been herein described and illustrated in or to explain the nature of the present invention, may be made by those skilled in the art white still remaining within the principles and scope of the invention.

What is claimed is:

1. A method for distracting a femoral head from an acetabulum of a hip joint, comprising:
    accessing the interior of a capsule surrounding the femoral head and acetabulum, the acetabulum being moveably sealed to the femoral head by a labrum;
    looping a device around the femoral head;
    guiding a balloon of the device to a gap between the femoral head and the acetabulum;
    securing the device to stabilize the balloon in the gap, wherein securing comprises pulling a distal end and proximal end of the device together in a proximal direction away from the joint; and
    inflating the balloon to distract the femoral head from the acetabulum.

2. The method of claim 1, wherein looping comprises pushing a distal end of the device around one side of the femoral head and recapturing the distal end at another side of the femoral head.

3. The method of claim 2 wherein the distal end of the device is recaptured by moving the distal end of the device into an opening.

4. The method of claim 3 wherein the device is movably mounted to a shaft, and further wherein the opening is formed in the shaft.

5. The method of claim 4 wherein the device is movably mounted in a lumen formed in the shaft.

6. The method of claim 5 wherein the lumen and the opening extend along an axis of the shaft.

7. The method of claim 1, wherein guiding comprises aligning two markers on the device to center the balloon in the gap.

8. The method of claim 1, wherein the device comprises an elongated wire with a precurved section for wrapping around the femoral head.

9. The method of claim 1, wherein the device comprises two additional side balloons, with one placed distally to the balloon, and one placed proximately to the balloon.

10. The method of claim 9, additionally comprising: tensioning the device to bring the two side balloons into a central compartment of the hip joint.

11. The method of claim 10, additionally comprising: inflating the two additional side balloons to further distract the femoral head from the acetabulum.

12. A method for distracting a femoral head from an acetabulum of a hip joint, comprising:
    accessing the interior of a capsule surrounding the femoral head and acetabulum, the acetabulum being moveably sealed to the femoral head by a labrum;
    looping a device around the femoral head, wherein the device comprises a balloon and two side balloons, with one side balloon placed distally to the balloon, and the other side balloon placed proximately to the balloon;
    guiding the balloon of the device to a gap between the femoral head and the acetabulum;
    securing the device to stabilize the balloon in the gap;
    inflating the balloon to distract the femoral head from the acetabulum; and
    tensioning the device to bring the two side balloons into a central compartment of the hip joint.

13. The method of claim 12, wherein looping comprises pushing a distal end of the device around one side of the femoral head and recapturing the distal end at another side of the femoral head.

14. The method of claim 13 wherein the distal end of the device is recaptured by moving the distal end of the device into an opening.

15. The method of claim 14 wherein the device is movably mounted to a shaft, and further wherein the opening is formed in the shaft.

16. The method of claim 15 wherein the device is movably mounted in a lumen formed in the shaft.

17. The method of claim 16 wherein the lumen and the opening extend along an axis of the shaft.

18. The method of claim 12, wherein guiding comprises aligning two markers on the device to center the balloon in the gap.

19. The method of claim 12, wherein securing comprises pulling a distal end and proximal end of the device together in a proximal direction away from the joint.

20. The method of claim 12, wherein the device comprises an elongated wire with a precurved section for wrapping around the femoral head.

21. The method of claim 12, additionally comprising: inflating the two side balloons to further distract the femoral head from the acetabulum.

* * * * *